United States Patent [19]

Barben, II

[11] 4,112,352
[45] Sep. 5, 1978

[54] ELECTROCHEMICAL REFERENCE CELL WITH IMPROVED LIQUID JUNCTION

[75] Inventor: Theodore R. Barben, II, Carson City, Nev.

[73] Assignee: Thomas Barben Instruments, Carson City, Nev.

[21] Appl. No.: 841,169

[22] Filed: Oct. 11, 1977

[51] Int. Cl.² .................................... G01N 27/42
[52] U.S. Cl. ......................... 324/30 R; 204/195 R
[58] Field of Search .............. 204/1 T, 195 T, 195 R; 324/29, 30 R, 30 B

[56] References Cited

U.S. PATENT DOCUMENTS

| 3,281,348 | 10/1966 | Schumacher | 324/30 R |
| 3,440,525 | 4/1969 | Cardeiro | 324/30 R |
| 3,666,652 | 5/1972 | Krauer et al. | 324/30 R |

Primary Examiner—M. Tokar
Attorney, Agent, or Firm—Nilsson, Robbins, Dalgarn, Berliner, Carson & Wurst

[57] ABSTRACT

An electrochemical reference cell has a reference electrode disposed at one end of a rigid hollow cylinder immersed in an electrolyte solution of known concentration. Different interlocking series of plugs, consisting of a material such as wood, with semipermeable, longitudinally extending capillaries, are fitted together in abutting relation to fill the hollow interior of the cylinder between the reference cell and the other end with one series longitudinally overlapping the other. The abutting end surfaces of adjacent plugs in each series are sealed to close off the capillary path between successive plugs, whereas the outer surface of the last plug in at least one series is left unsealed to be in contact with the test solution, so that circuitious ion transfer path is established between the reference cell and the test solution that passes tranversely through the longitudinal semipermeable capillary walls from the plugs in one series through adjacent plugs in the other.

16 Claims, 3 Drawing Figures

ELECTROCHEMICAL REFERENCE CELL WITH IMPROVED LIQUID JUNCTION

BACKGROUND OF THE INVENTION

1. Field of the Invention

The invention relates to electrochemical reference cells, and more particularly, to systems incorporating such reference cells with improved liquid junctions for use in continuous monitoring of process streams.

2. Prior Art

Electrochemical reference cells used in pH or other specific ion meters typically employ calomel or other metal-metal salt reference electrodes immersed in a suitable electrolyte of known concentration that communicates through a liquid junction with the sample fluid being monitored. The liquid junction maintains a conductive bridge between the reference cell electrolyte and the liquid sample to provide a common potential in both solutions, while mixing of the two solutions is restricted to avoid changes in the electrolyte concentration that would vary the reference cell potential.

With earlier pH meters used for laboratory testing, the liquid junction was simply a minute opening in a glass or ceramic barrier through which ion communication between the two solutions could be established. However, with prolonged usage, the single opening junctions could readily be clogged. As a result, larger liquid junctions were developed using porous ceramic barriers, asbestos wicks, ground glass joints, or in some cases, an area of thin cracks produced by fusing together two glass formulations with different coefficients of expansion. However, to minimize mixing of the reference cell electrolyte with the sample fluid with these larger junctions, two or more liquid junctions placed in series were often required so that the reference cell electrolyte communicated through an intermediate salt bridge with the sample liquid. Nevertheless problems were still encountered in maintaining the liquid junction open for continuous process control use. Even with the larger, liquid junctions the small openings would eventually be plugged either by solid impurities in the process stream or by crystals formed within the reference cell where an electrolyte or saturated salt solution was used.

As disclosed in U.S. Pat. No. 3,440,525, issued to Charles P. Cardeiro, this problem was alleviated by the use of relatively large diameter wooden or porous ceramic plugs that established the liquid junction through minute capillaries extending longitudinally between the sample and reference fluids. The wooden plug was most effective and could be used wherever the cellulose structure was not dissolved or otherwise incompatible with the chemical solutions on either side of the junction. The numerous individual capillaries extending over the entire surface of the plug were not all readily clogged even under the worse sample process stream conditions, whereas the conductive bridge between the two liquids was maintained through the end walls of adjacent capillary cells the basic dilemma remained. Eventually, either the plug surface became completely covered with solid deposits or the salt ion exchange through the cell walls depleted the electrolyte concentration in the reference cell causing meter drift. Moreover, although the plug surface area could be increased to retard fouling by impurities, the resulting higher rate of ion exchange through additional capillary paths would more rapidly deplete the electrolyte concentration.

BRIEF SUMMARY OF THE INVENTION

This invention employs a unique liquid junction structure that has large end surfaces exposing a multitude of semipermeable cell openings to the sample stream and to the reference cell so as to resist fouling by solid deposits, while also providing a high resistance ion exchange path between the two fluids that maintains a constant electrolyte concentration in the referencee cell. Thus large diameter plugs can be used without excessive ion exchange rates diluting the electrolyte concentration in the reference cell.

In the preferred embodiments, the liquid junction device consists of longitudinally overlapping series of wooden plugs, or other semipermeable cell structures, abutting one another to fill the interior of a rigid elongated plastic cylinder with one closed end. Each of the plugs is cut so that the capillaries within the wooden structure extend longitudinally along the path between the opposite ends of the elongated enclosure, and the abutting surfaces of adjacent plugs in each series are sealed to close off direct communication between capillaries in successive blocks. In this manner, the ion transfer path between the solutions is directed transversely through the longitudinally aligned cell walls from one plug in a series through the interface with abutting surfaces of the overlapping plugs in the adjacent series to define a circuitous conductive bridge route passing through numerous semipermeable cell walls.

In one preferred form, the reference cell employing a liquid junction in accordance with the invention incorporates a conventional pH sensitive glass electrode in a pH metering assembly especially suited for prolonged usage with cooling water process streams. The liquid junction employs a series of toroid shaped hardwood plugs that are inserted to fit snugly within the rigid plastic cylinder with their central bores longitudinally aligned to slidably receive the elongated glass sensing electrode extending through an opening in the closed end of the container. Each plug also has a pair of side apertures, axially displaced on opposite sides of the central bore, for receiving a series of solid cylindrical hardwood plugs or dowels. The internal capillary structure of the wood in both series of plugs extends longitudinally, and the abutting end surfaces of adjacent plugs are sealed with an epoxy resin or other adhesive sealant to close off the longitudinal fluid path between successive plugs. The solid plugs are inserted midway into one of the side apertures in successive pairs of toroidal plugs on alternate sides of the central bore, and the resin or other sealant fills the intervening spaces within the side apertures to seal off the fluid path between successive dowels on each side.

The metal-metal salt reference electrode, typically a silver-silver chloride wire, extends through the closed end of the plastic cylinder into a cavity defined by one of the side apertures in the toroidal plug at that end. This cavity is filled with the appropriate electrolyte or salt bridge solution, such as saturated potassium chloride and, if desired, an excess of salt crystals to maintain a saturated concentration. The same solution impregnates the entire wooden structure within the cylinder to form the conductive bridge between reference cell and the sample. In this manner, a convoluted ion exchange path is established from the sample solution in contact with the exposed outer surface of the plug at the open end of the plastic cylinder, passing through the first dowel on one side to the next toroidal plug, and then through the wood around the glass electrode to the next dowel inserted into the other side aperture, and so on through each successive toroidal plug and dowel, finally reaching the reference cell cavity.

In a simplier embodiment involving only a reference cell assembly without an integral sensing electrode, a series of simple toroid shaped hardwood plugs are slidably received within the rigid plastic cylinder with their central bores aligned to receive a series of solid cylindrical wooden plugs or dowels. An epoxy adhesive seals off the abutting end surfaces of the successive wooden plugs in each series. The dowels arranged in a overlapping relationship to extend approximately midway into the central bore on either side of the two successive toroid shaped plugs, and the reference electrode extends into the opening provided within the cavity formed by the outer half of the central bore of the toroid plug at the closed end of the cylinder. As in the previously described embodiment, the entire wooden structure is impregnated with the appropriate salt bridge solution and the reference cell cavity filled with an appropriate electrolyte solution of known concentration. The ion exchange paths is thus established from the exposed surface of the dowel at the open end of the cylinder, through the adjacent toroid shaped plug into the next dowel in the series, and so on, until reaching the reference cell cavity at the closed end.

DETAILED DESCRIPTION

Figure 1:
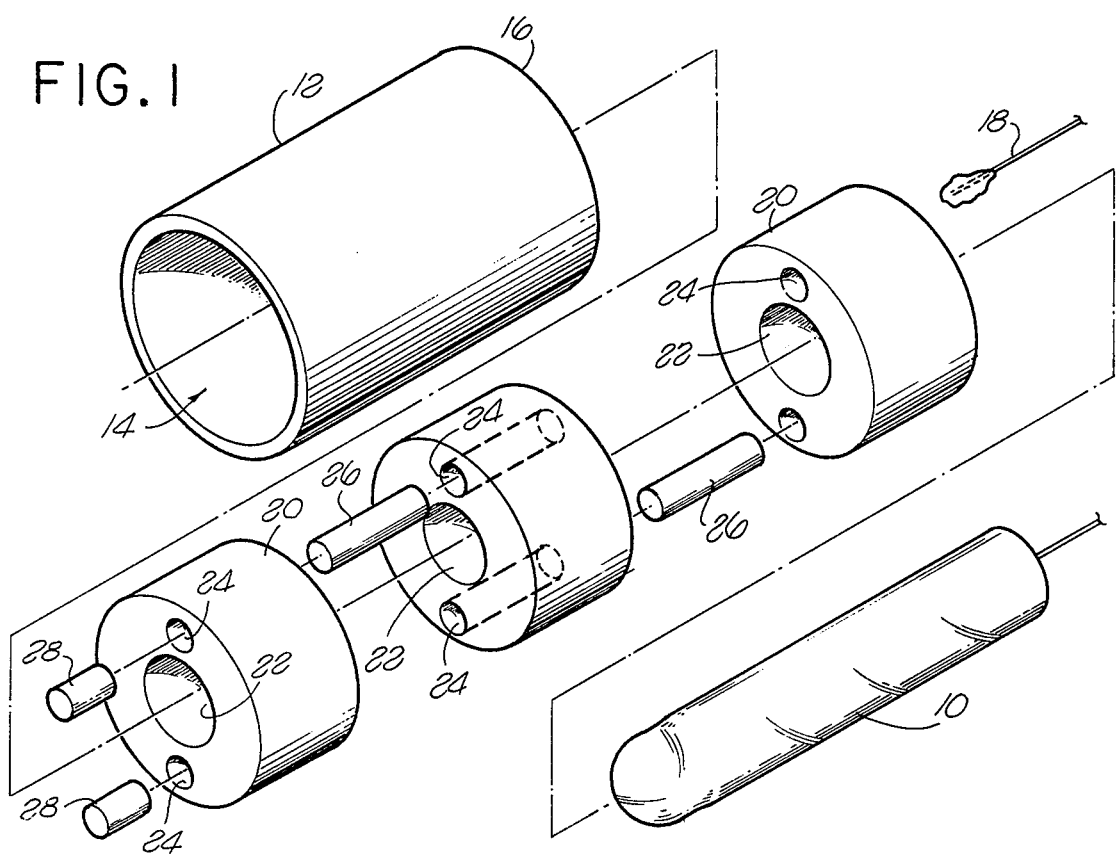
FIG. 1 is in an exploded perspective view showing the individual components of one preferred form of the invention that incorporates a conventional pH sensitive electrode arranged in the proper order for assembly.
Figure 2:
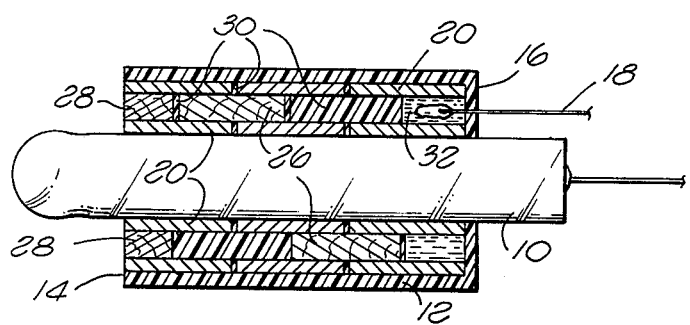
FIG. 2 is a cross-sectional view of the preferred embodiment of the invention employing the components illustrated in FIG. 1; and, FIG. 3 is a cross-sectional view of another preferred form of the invention for providing an electrochemical reference cell with a separate sensing electrode.

Referring now to FIGS. 1 and 2, the preferred form of pH meter assembly has a conventional glass sensing electrode 10 that extends through a rigid cylindrical container 12 which houses the other components. Typically, the container 12 is formed with high density polyethylene plastic or other material that has the desired structural rigidity and is inert or otherwise chemically compatible with the electrochemical system. The container 12 has an open end 14 that communicates with the sample fluid and a closed end 16 is sealed around the glass electrode 10 inserted through a central opening. Also a reference electrode wire 18, which is typically the conventional silver-silver chloride or a calomel type electrode, extends through a small opening in the closed end 16 and is sealed in place.

A liquid junction between the reference electrode 18 and the sample stream at the open end 14 is established through two overlapping series of interlocking plugs that fill the interior of the container 12 surrounding the glass electrode 10. In the specific embodiment illustrated, the first series consist of three thick walled hollow cylindrical or toroid shaped larger plugs 20 that fit snugly within the cylinder 12, each having a central bore 22 that slidably receives the axially disposed glass electrode 10 at the center of the housing. Each of these toroidal plugs 20 also has a pair of longitudinally extending side apertures 24 axially displaced on opposite sides of the central bore 22.

The second series of plugs are solid cylinders 26 and 28 that are slidably insertable into the side apertures 24 of the toroidal plugs 20. Two of solid cylindrical plugs 26 have approximately the same longitudinal dimensions as the larger toroidal plugs 20 for insertion midway into the side apertures 24 thus overlapping the longitudinal extent of adjacent pairs of toroidal blocks 20. Only one solid plug 26 is used between each adjacent pair of toroidal blocks 20 with successive ones on alternate sides of the central bore 22. The shorter cylindrical plugs 28 are only half as long and are inserted into the outer portion of both side apertures 24 in the toroidal block 20 located at the open end 14 of the rigid cylinder housing 12.

In the devices produced for cooling water control systems, the plugs 20, 26 and 28 are all preferably formed of a suitable hardwood, such as ash or birch with the grain oriented so that the elongated capillary cells extend substantially longitudinally in parallel with the central axis of the cylinder 12. In a typical assembly, the diameter of the toroidal plugs 20 has been three-quarters inch with the smaller overlapping plugs 26 and 28 being ¼ to ⅜ inch in diameter, depending upon the available rim thickness. For the most part, available wood dowel stock can be employed if care is taken in selecting the proper grain orientation. Each plug is cut to the desired length, and the central bore 22 and side apertures 24 in the toroidal plugs 20 drilled to fit the glass electrode 10 and the smaller dowels 26 and 28, respectively.

During assembly, each of the plugs 20, 26 and 28 has its interior transverse surfaces coated with an appropriate epoxy or other adhesive sealant 30 that forms a fluid type seal between adjacent plugs in each series. Also, the space within the side apertures 24 opposite those containing the overlapping dowel plugs 26 are filled with the epoxy or adhesive 30 to prevent direct fluid communication between the adjacent toroidal plugs 20, as shown in FIG. 2. However, the end of one side aperture 24 in the toroidal plug 20 at the closed end of the rigid cylinder 12 is left unfilled to define a reference cell cavity 32 into which the reference cell electrode 18 extends through the closed end 16 of the cylinder 12. The remainder of this side aperture 24 defining the reference cell cavity 32 is filled with the epoxy sealant 30, but the other side aperture 24 has one of the longer solid plugs 26 inserted midway, and the unfilled space between the sealed end of the solid plug 26 and the closed end of the rigid container 12 provides a reservoir cavity for storing additional electrolyte or salt bridge solution. In most pH meter assemblies, the convention reference half cell has a silver-silver chloride electrode immersed in a saturated potassium chloride electrolyte, and an excess of undissolved potassium chloride salt can be stored within the vacant portion of the side aperture 24 opposite the one containing the reference electrode 18, thereby maintaining the saturation of the reference cell electrolyte by ion exchange through the capillary structure of the plug 20. Of course, other available reference half cell systems such as those employing the mercury-calomel electrode can be similarly implemented.

Figure 3:
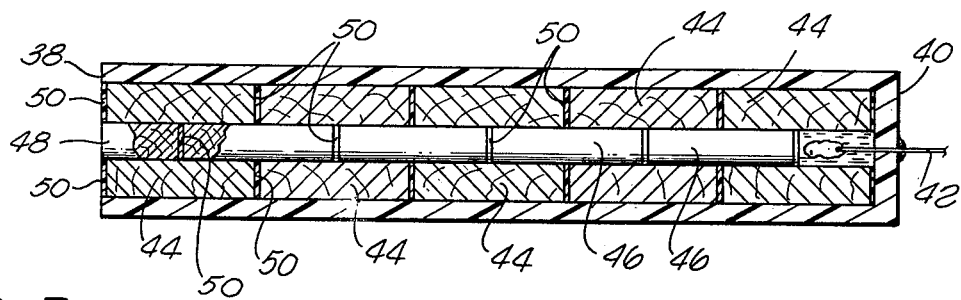

Referring now to FIG. 3, a simplier form of the invention is useful in improving the operational characteristics and longevity of a reference cell with a separate sensing electrode. In this instance, an elongated rigid cylindrical container 36 has its open end 38 communicating with the sample fluid and a reference electrode 42 inserted and sealed in place through its closed end 40. The interior of the cylindrical container 36 is filled by a first series of hollow thick walled cylinders or toroidal shaped plugs 44 with a second series of solid cylindrical plugs or dowels 46 and 48 slidably inserted into their central bores to longitudinally overlap successive toroidal plugs 44. The overlapping solid plugs 46 each have a longitudinal dimension substantially the same as that of the toroidal plugs 44 to overlap midway on either side. A final solid plug 48 about half as long is inserted into the outer portion of the central bore in the toroidal plug 44 at the open container end 38 with its outer surface exposed to the sample fluid. Preferably the surrounding outer surface of the outer toroidal plug 44 is coated with a layer of epoxy or other adhesive sealant to close off direct fluid communication of the sample with the interior cell structure. Similarly, the abutting end surfaces between both series of overlapping plugs 44, 46 and 48 are coated with the epoxy or adhesive sealant to prevent direct fluid communication between the interior cell structures of successive plugs. At the closed end of the rigid tubular container 36, the final solid dowel plug 46 is inserted only about halfway into the central bore of the innermost toroidal plug 44, so that the remaining half of the central bore form an electrolyte reservoir cavity surrounding the reference electrode 42, and the adjacent end surface of the dowel 46 is coated with the epoxy or adhesive sealant to prevent direct fluid communication from this reservoir into the interior cell structure of the final dowel 46.

As in the other previous embodiment of FIGS. 1 and 2, the reference cell structure of FIG. 3 typically employs hardwood plugs 44, 46 and 48 that may be selected from available dowel stock with appropriate care in selecting the grain orientation so that the interior capillaries are substantially longitudinally aligned. In both embodiments, the inner diameter of the various components are made slightly larger than the outer diameter of the component to be received within so that the parts are easily slidable into position within one another. In the assembly, the components are assembled together with the epoxy or adhesive sealant applied to the indicated surfaces. Almost any conventional two part epoxy can be used as a sealant, as well as most sorts of glue, as long as they are chemically compatible with the electrolyte and sample stream solution and cured to form a uniform fluid tight layer. A few that have proved successful are Hobby Formula #2 by Petit Paint Company of Belleville, N.J.; Resin #86 with catalyst #C-321 from Epoxylite Corporation of Buffalo, N.Y.; and the adhesive product sold under the trademark "E-POX-E" from Woodhill Chemical of Cleveland, Ohio.

After assembly and adequate curing of the sealant material, the entire structure is placed for relatively long period in a vacuum chamber to insure that substantially all of the residual moisture and gas within the wood is removed. Thereafter, the entire assembly is immersed, preferably under high pressure, in a bath containing the reference cell electrolyte or salt bridge solution until the wood is thoroughly impregnated throughout the entire length of the container and the reference cell cavity is filled. Depending upon the dimensions and the type of wood involved, the vacuum and pressure immersion process might require anywhere from a few hours to several days to obtain complete impregnation. If solid salt cyrstal are desired in the reservoir, these must be introduced during the initial assembly.

The hardwood plug described in connection with the preferred embodiments used in cooling water control systems are ideal because of the internal capillary structure wherein the closely packed elongated cells provide multiple semipermeable layers overlying one another in the transverse direction. Normally, cooling water control systems operate to maintain a substantially neutral pH to avoid acidic corrosion of the pipes or scaling from too alkaline a condition. Of course, wood may not be compatible with other sorts of process streams where a more acid or alkaline condition, or other chemical properties of the fluid, could attack the wood. In such instances, the plugs might be formed with a closed cell, hydrophillic plastic foam material or similarly inert material with an internal cell structure. Materials like cellulose acetate or butyrate, phenolic, or polyurethane foams could be adapted using known techniques to simulate the effects of the wood in providing successive semipermeable layers.

In operation, the conductive bridge for achieving the liquid junction ion exchange is established through the exposed surface of one or more of the plugs at the open end of the container but are exposed to the sample stream. Since the end of the capillaries or other cell structure is closed off by the sealant, the path must be directed transversely through the multiple semipermeable layers across the interface between the overlapping plugs. The conductive bridge is thus directed through numerous separate layers of semipermeable material in traveling a circuitous path from a plug in one series transversely to the overlapping plug in the adjacent series with each successive layer adding to the total resistance, whereas the exposed surface of the outermost plug in contact with the sample stream affords a multitude of tiny capillary openings that resist fouling by impurities.

Additionally, with the wooden plugs described in connection with the preferred embodiments herein, the absorption of the salt bridge solution causes swelling of the wood that expands its dimensions in the transverse direction thus causing the plugs to be tightly pressed against one another, as well as against the central glass electrode in the embodiment of FIG. 2, and against the inside of the rigid cylindrical container 12, or 36 for the second embodiment of FIG. 3. Significantly, the impregnation with the fluid causes little or no longitudinal expansion of the plug elements.

In comparing the embodiment of FIGS. 1 and 2 with that of FIG. 3, it should be noted that the former provides significant advantages in achieving a high resistance conductive bridge path with a shorter series of individual plugs. This is because of the alternate placement of the dowel plugs 26 so that the path is directed through a substantial thickness of wood and the large toroidal plugs 20 surrounding the glass electrode 10 and the central bore 22. By this means, an enhanced effect can be achieved with reduced overall dimension.

While the cylindrical shapes of the interlocking plugs and container is most advantageous in achieving a tight fit between the components, other interlocking plug shapes might be employed, such as rectangular blocks or curved plugs with the congruent convex and concave abutting surfaces.

I claim:

1. A reference cell for use in measuring the pH of a sample fluid stream comprising:
   an elongated rigid enclosure having an open end exposed to said sample fluid and a closed end;
   at least two transversely adjacent longitudinal series of plug means disposed in longitudinally overlapping relationship with an interlocking fit to fill the open end of said enclosure;
   a reference cell containing a reservoir electrolyte solution in contact with said cell means at the opposite end of said enclosure and separated from said sample fluid by said plug means;
   each of said plug means consisting of successive longitudinally disposed layers of semipermeable material permeated with said electrolyte solution;
   an impermeable seal between abutting transverse end surfaces of said plug means in each series and joined to the surrounding longitudinal surfaces of the overlapping adjacent plug means and said enclosure at approximately midway between the end portions of the adjacent series, the outer end surface of at least one plug means exposed to said sample fluid at the open end being unsealed to provide fluid communication between said layers;
   whereby an ion transfer path between said sample fluid stream and said electrolyte solution is established transversely through successive layers of said semipermeable material in passing between the longitudinal surfaces of the plug means in one series to the abutting overlapping longitudinal surfaces of adjacent plug means in the other series.

2. The reference cell of claim 1 wherein:
   each of said plug means is solid wood with the grain oriented so that elongated interior capillary cells are substantially aligned longitudinally.

3. The reference cell of claim 2 wherein:
   said impermeable seal consists of a coating of epoxy adhesive applied to the abuttiing transverse end surfaces of adjacent plug means.

4. The reference cell of claim 3 wherein:
   said reservoir of electrolyte solution consists of a saturated salt solution.

5. The reference cell of claim 4 wherein:
   said saturated salt solution consists of an aqueous chloride salt solution with an excess of undissolved salt immersed therein, said sealed enclosure having its end opposite said open end closed to form a reference cell cavity surrounding a reference electrode within.

6. The reference cell of claim 1 wherein:
   the two transversely adjacent longitudinal series of plug means consist of an inner series of solid cylindrical plugs inserted slidably received into the longitudinal bore of an outer series of longitudinally aligned toroid shaped plugs; and,
   said rigid enclosure being an elongated tube of impermeable material for slidably receiving said toroid shaped plugs.

7. The reference cell of claim 6 wherein:
   said inner series of solid cylindrical plugs consists of wooden dowels with the grain oriented to align the interior capillary cells in a substantially longitudinal direction;
   said outer series consists of toroid shaped wooden sections with a central bore diameter matching the diameter of the dowels; and,
   said elongated sealed enclosure comprises a plastic tube having an inner diameter matching the outer diameter of said tubular wooden sections.

8. The reference cell of claim 7 wherein:
   said impermeable seal consists of a coating of epoxy adhesive applied to the abutting transverse end surface os adjacent cell means.

9. The reference cell of claim 8 wherein:
   said reservoir of electrolyte solution consists of a saturated salt bridge solution.

10. The reference cell of claim 9 wherein:
    said saturated salt bridge solution consists of an aqueous chloride salt solution with an excess of undissolved salt immersed therein, said rigid enclosure having its closed end defining a reservoir cavity surrounding a reference electrode with the central bore of the adjacent toroid shaped wooden section.

11. The reference cell of claim 1 wherein:
    said transversely adjacent longitudinal series of plug means consist of a first series of toroidal wooden sections longitudinally aligned with a central bore for slidably receiving a tubular pH sensitive glass electrode, each of said toroidal wooden sections having a pair of longitudinal side apertures uniformly displaced from and on opposite sides of said central bore, and said adjacent series of plug means consists of solid wooden dowels slidably inserted into the longitudinally aligned holes of said toroidal wooden sections, the grain of the wood in both series being oriented to lontitudinally align the elongated capillaries within the wood.

12. The reference cell of claim 11 wherein:
    said impermeable seal consists of a coating of epoxy adhesive applied to the abutting transverse end surfaces of adjacent plug means.

13. The reference cell of claim 12 wherein:
    said reservoir of electrolyte solution consists of a saturated salt solution.

14. The reference cell of claim 13 wherein:
    said saturated salt solution consists of an aqueous chloride salt solution with an excess of undissolved salt immersed therein, said rigid enclosure having its closed end defining a reservoir cavity surrounding a reference electrode.

15. The reference cell of claim 14 wherein:
    said elongated rigid enclosure comprises a sealed plastic tube having an inner diameter matching the outer diameter of said toroidal wooden sections.

16. The reference cell of claim 11 wherein:
    said solid wooden dowels are inserted midway into the side apertures of only alternate pairs of adjacent toroidal sections, whereby a conductive bridge path is established from the dowel on one side through the toroidal wood section to the dowel on the other side.

* * * * *